United States Patent
Hunt

(10) Patent No.: US 8,378,326 B2
(45) Date of Patent: Feb. 19, 2013

(54) X-RAY SHIELD

(75) Inventor: Kenneth Charles Hunt, Harlow (GB)

(73) Assignee: Kenex (Electro-Medical) Limited, Essex (GB)

(*) Notice: Subject to any disclaimer, the term of this patent is extended or adjusted under 35 U.S.C. 154(b) by 92 days.

(21) Appl. No.: 13/002,516

(22) PCT Filed: Jul. 3, 2009

(86) PCT No.: PCT/GB2009/050784
§ 371 (c)(1), (2), (4) Date: Jan. 21, 2011

(87) PCT Pub. No.: WO2010/001177
PCT Pub. Date: Jan. 7, 2010

(65) Prior Publication Data
US 2011/0103555 A1  May 5, 2011

(30) Foreign Application Priority Data
Jul. 4, 2008 (GB) .................................. 0812280.6

(51) Int. Cl.
*G21F 3/00* (2006.01)
(52) U.S. Cl. .................................. 250/519.1; 250/515.1
(58) Field of Classification Search ............... 250/505.1, 250/515.1, 519.1; 378/203
See application file for complete search history.

(56) References Cited

U.S. PATENT DOCUMENTS

| 3,723,743 | A | | 3/1973 | Brackenbrough et al. |
| 5,006,718 | A | * | 4/1991 | Lenhart ...................... 250/519.1 |
| 5,417,225 | A | * | 5/1995 | Rubenstein et al. .......... 128/849 |
| 5,981,964 | A | * | 11/1999 | McAuley et al. .......... 250/515.1 |
| 2006/0124871 | A1 | | 6/2006 | Ballsieper |
| 2007/0252095 | A1 | * | 11/2007 | Magram ................... 250/515.1 |

FOREIGN PATENT DOCUMENTS

| CA | 2170635 A1 | 3/1995 |
| DE | 11 07 889 B | 5/1961 |
| DE | 1 516 420 A1 | 8/1969 |
| DE | 3326880 A1 | 2/1985 |
| DE | 297 06 321 U1 | 6/1997 |
| WO | 00/74072 A1 | 12/2000 |
| WO | 2007/103581 A2 | 9/2007 |
| WO | WO 2007103581 A2 * | 9/2007 |

OTHER PUBLICATIONS

International Search Report from PCT/GB2009/050784 dated Oct. 28, 2009 (4 pages).
Written Opinion from PCT/GB2009/050784 dated Oct. 28, 2009 (5 pages).
UK Intellectual Property Office Search Report from Application No. GB0812280.6 dated Oct. 20, 2008 (2 pages).

* cited by examiner

*Primary Examiner* — Robert Kim
*Assistant Examiner* — David E Smith
(74) *Attorney, Agent, or Firm* — Osha Liang LLP

(57) ABSTRACT

An X-ray shield for a horizontal X-ray procedure table includes a horizontal support bar for attachment thereto a first depending X-ray opaque curtain and a second support bar, the second support bar being moveably attached to the horizontal support bar to enable movement of the second support bar in both horizontal and vertical directions.

20 Claims, 5 Drawing Sheets

X-RAY SHIELD

TECHNICAL FIELD

The invention relates to X-ray shields for attachment to X-ray procedure tables to protect a physician from unwanted radiation during a procedure.

BACKGROUND

During certain interventional proceedings, e.g. those involving the insertion of an intravascular catheter, patients are required to lay supine on an X-ray procedure table. The physician then inserts an intravascular catheter through a small incision made in the patients arm or groin, which is then guided to the desired location.

To facilitate this process the tip of the catheter is X-ray opaque, allowing the physician to guide the catheter under fluoroscopic observation.

Fluoroscopic observation is a real-time imaging technique involving placing the patient between an X-ray emitting tube and an image intensifier or digital detector. Typically the X-ray tube is carried by the lower end of a C-shaped arm with the detector positioned at the other end. Such C-arms are freely moveable to permit a wide range of radiographic views of the patient.

During a procedure the physician passes the catheter through the patient and tracks its location on a monitor, which gives a visual representation of the radiation received by the digital detector. Typically the X-ray tube is located underneath the table and the physician moves the C-arm accordingly to continue tracking the location of the catheter as the procedure continues.

Although the majority of the X-rays pass through the table, to the patient and to the detector, inevitably there is some scatter. As such interventional procedures often take an extended time to complete, this has the potential to may expose the physician to a significant amount of radiation.

To reduce exposure to radiation, a number of X-ray protection table mounted shields have been developed, for example those shown in U.S. Pat. No. 5,006,718 and U.S. Pat. No. 5,981,964, which involve a flexible X-ray curtain positioned between the physician and patient and extending from the side of the table to the floor. Such shields have a horizontal hinge to allow the shield to be repositioned to allow for the passage of a C-arm during a procedure.

However, inevitably there will be occasions where, for whatever reason, the shield is not repositioned during movement of the C-arm, resulting in a collision between the C-arm and shield. For example, the position of the shield may not be apparent if it is covered with sterile drapes, as often happens. Additionally the physician will be concentrating on the procedure to hand and may not realise that movement of the C-arm may result in a collision.

Such C-arms are often fitted with collision detection devices for safety reasons, however even though this may reduce the risk of damage to equipment, the procedure will be interrupted and may result in its cancellation.

SUMMARY OF THE INVENTION

The invention relates to an X-ray shield for a horizontal X-ray procedure table, comprising a horizontal support bar for attachment to a first depending X-ray opaque curtain, and a second support bar, the second support bar being moveably attached to the horizontal support bar to enable movement of the second support bar in both horizontal and vertical directions.

Thus, if a C-arm inadvertently collides with the X-ray shield from below, the second support bar is pushed out of the way irrespective of the direction of movement of the C-arm.

Typically a depending X-ray opaque curtain is attached to the second support bar. This may be a continuation of the first depending curtain or could be a separate curtain. Such curtains are typically flexible and drapable. Additional X-ray curtains may be attached to the support bar, e.g. extending upwards from the bar. Such upwardly extending curtains may be rigid in construction.

Typically the horizontal support bar is for attachment to a horizontal accessory rail on the side of a typical X-ray procedure table. The shield can therefore be fitted to existing tables to improve their performance without requiring a replacement table. Typically the X-ray opaque curtain or curtains are attached to the shield to form a complete unit for attachment to a table in the above manner.

Such X-ray procedure tables often do not have a constant width along their whole length and typically become narrower near the head of the table with the width contracting in sudden steps. In order for the shield to remain in close contact with the side of such a table, the horizontal support bar may be horizontally moveable, e.g. by comprising a hinge for horizontal movement of two rigid horizontal bar portions. This allows it to follow snugly any sudden contractions of the width of the table.

Preferably the second support bar is hingedly attached to the horizontal support bar, e.g. by means of a single multi-directional hinge or by means of a vertical hinge and a separate horizontal hinge. Preferably a vertical hinge and a separate horizontal hinge are used which may be together in a single unit or separated by a short connecting portion.

In a preferred embodiment, the second support bar is biased to return to a horizontal orientation under gravity. This enables the shield to take a horizontal orientation along its length under normal conditions. After a C-arm inadvertently collides with the second support bar it pushes the second support bar upwards and possibly also to the side. After the situation has been remedied the second support bar returns to horizontal under its own weight.

Preferably the shield is adapted so that it can be to be fitted to either side of an X-ray procedure table. This may, for example, be achievable by rotating the shield through 180°, maintaining the second attachment bar at the head end of the X-ray procedure table.

If this feature is to be combined with that of the second support bar being arranged to return to a horizontal orientation under gravity, then special considerations must be made for this. For example, the vertical hinge may be adaptable to permit movement away from horizontal in only one chosen direction, according to the position of a stopping pin in the hinge, which the user can position as desired.

BRIEF DESCRIPTION OF THE DRAWINGS

The invention will now be described, by way of illustration, with reference to the following figures, in which.

DETAILED DESCRIPTION

Figure 1:
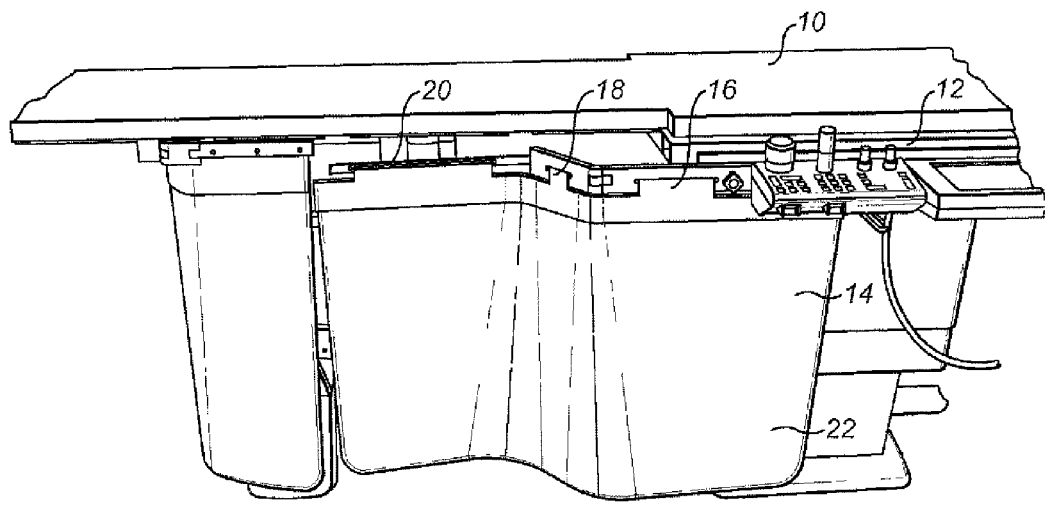
FIG. 1 is an image of an X-ray procedure table with a known X-ray shield attached.

FIG. 1 shows an X-ray procedure table 10 comprising a horizontal accessory rail 12 which has attached to it a known design of X-ray shield 14. The shield 14 can be seen to be made up of three horizontally hinged together support arms 16, 18, 20. Depending from the support arms is an X-ray opaque curtain 22.

Figure 2:
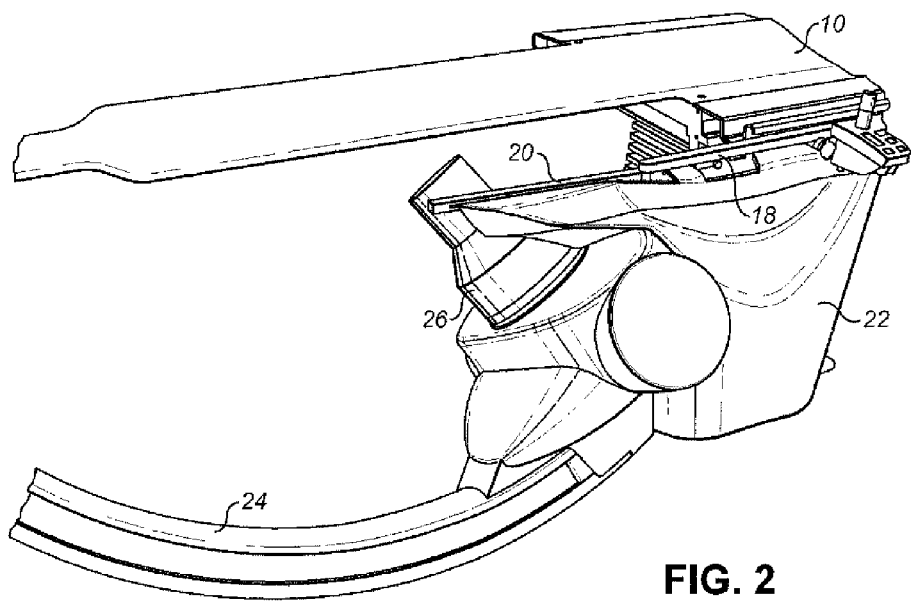
FIG. 2 is an image of the prior art arrangement as shown in FIG. 1 with a C-arm colliding with the shield.

FIG. 2 shows the arrangement as shown in FIG. 1 but where a C-arm 24 having at one end an X-ray emitter 26 is in collision with the horizontally hinged support arm 20. In this case either the C-arm will stop moving due to it possessing a colision detection device or the shield will be damaged. In either event the procedure will at least be interrupted and may need to be cancelled.

Figure 3:
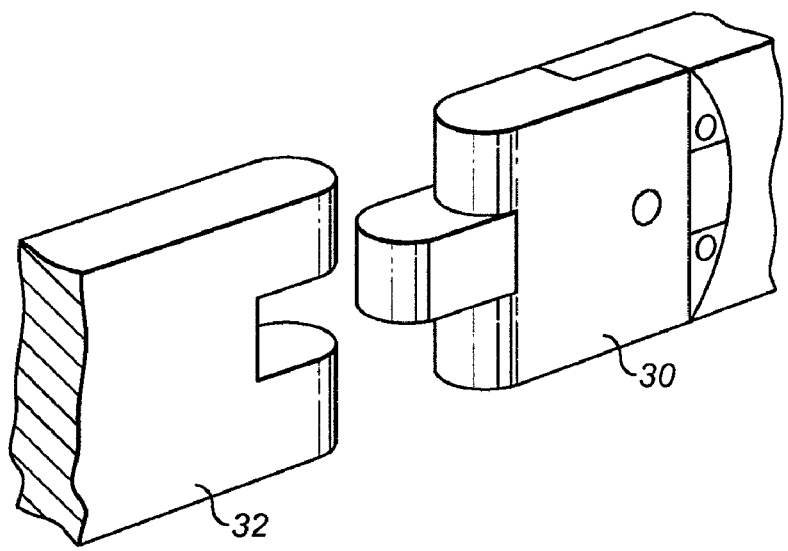
FIG. 3 is a perspective view of a horizontally hinged horizontal support bar.

FIG. 3 shows two portions 30, 32 of a horizontal support bar according to the invention. The two portions are connected by a horizontal hinge, as is known in the prior art.

Figure 4:
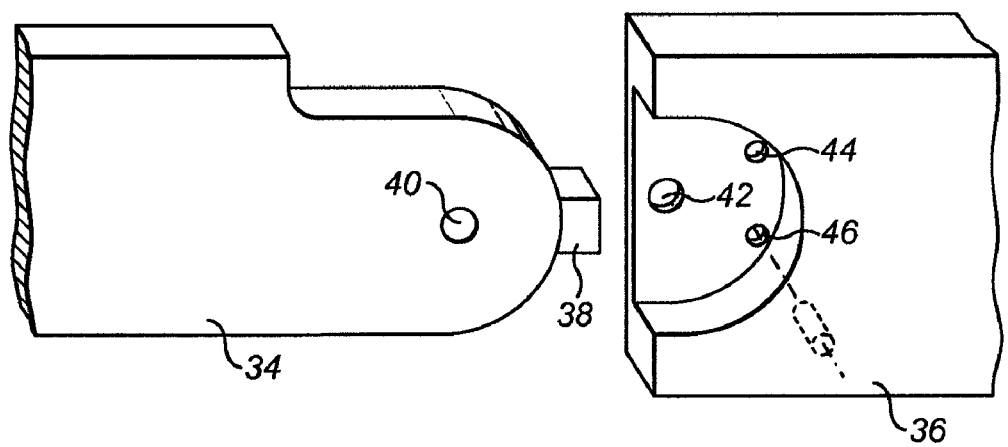
FIG. 4 is a perspective view of a vertical hinge for use in the present invention.

FIG. 4 shows a second support arm 34 according to the invention for connection with a connecting component 36. Support arm 34 ends with a stop 38. The support arm 34 is connected to connecting component 36 by a locating pin (not shown) passing through holes 40 and 42.

The connecting component 36 also has additional thru-holes 44, 46 in which can be placed a stopping pin (not shown). When the support arm 34 is connected to connecting component 36 a stopping pin is placed in thru-hole 44 to keep the second support arm 34 horizontal.

With the design shown in FIGS. 3 and 4 it can be seen that the arrangement can be rotated through 180° so that it may be used on either side of an X-ray procedure table. In this case the stopping pin must be removed from thru-hole 44 and put into thru-hole 46.

Figure 5A:
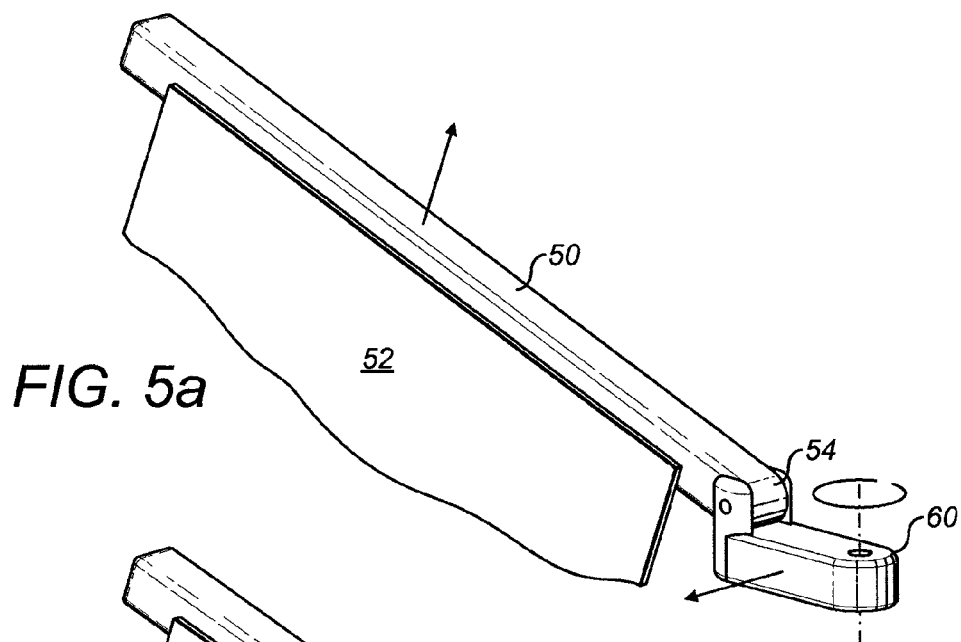
FIGS. 5a to c are perspective views of three types of vertical and horizontal hinges for use in the present invention.
Figure 5B:
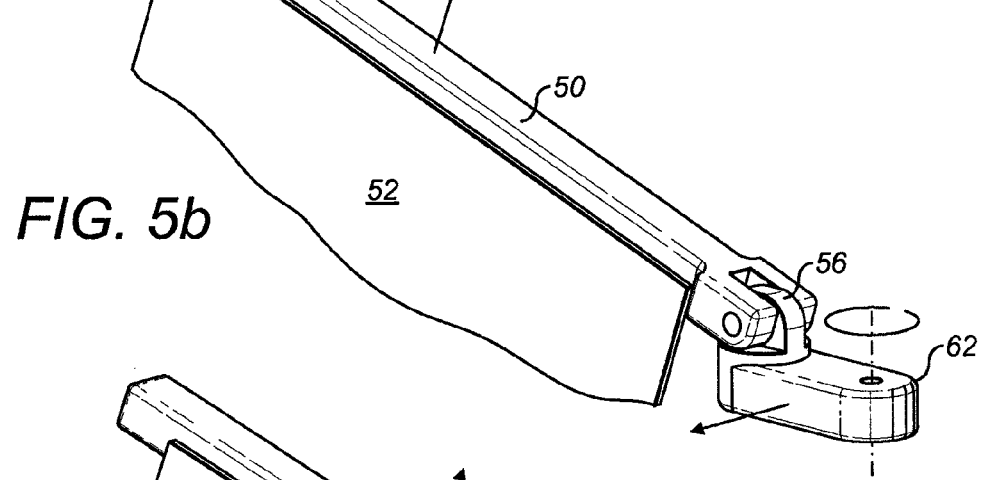
Figure 5C:
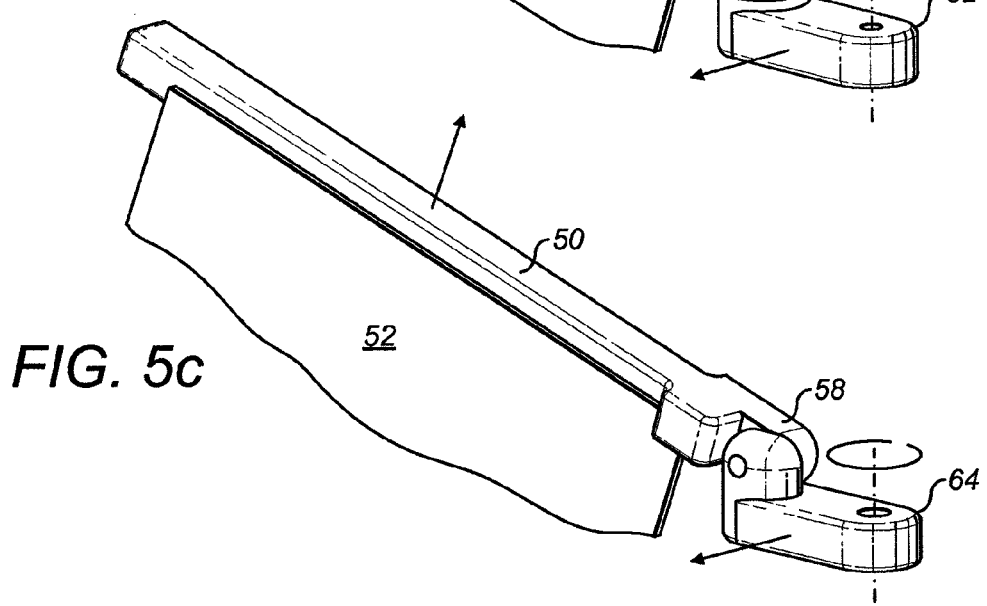

FIGS. 5a to c each show a second support bar 50 having a depending X-ray opaque curtain 52, for connection to a horizontal support bar (not shown) by both vertical hinge 54, 56 58 and a horizontal hinge 60, 62, 64.

Figure 6A:
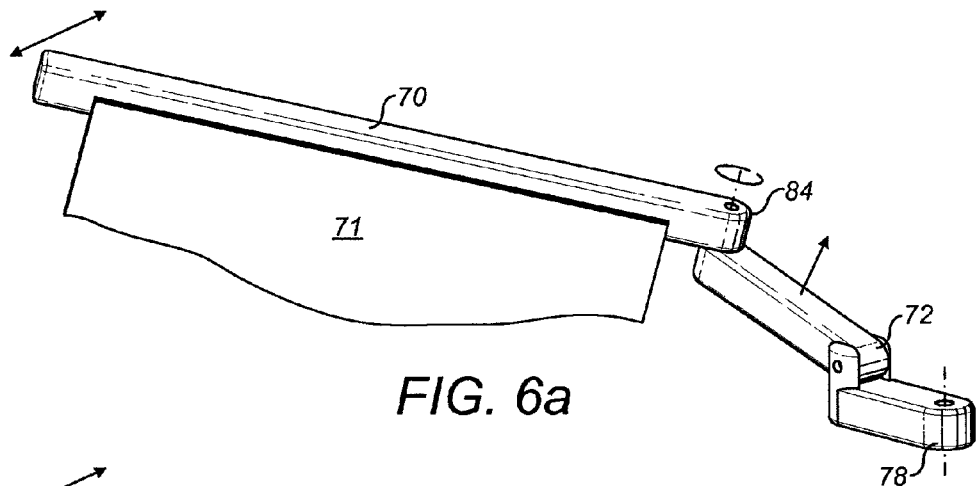
FIGS. 6a to c are perspective views of three more types of vertical and horizontal hinges for use in the present invention.
Figure 6B:
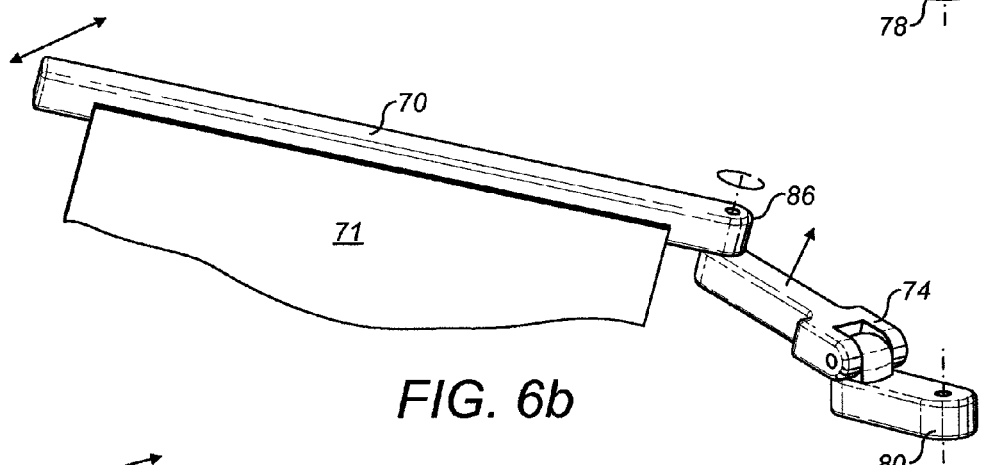
Figure 6C:
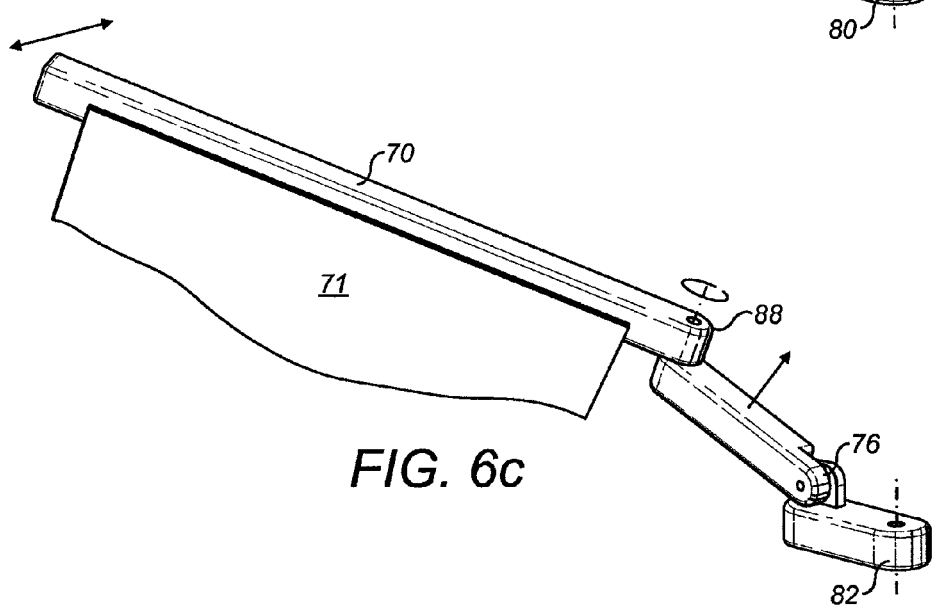

Likewise FIGS. 6a to c show a second support bar 70 having a depending X-ray opaque curtain 71, for connection to a horizontal support bar (not shown). The support bar comprises a vertical hinge 72, 74, 76 and horizontal hinge 78, 80, 82. In this case the second support bar also comprises an additional horizontal hinge 84, 86, 88.

Figure 7:
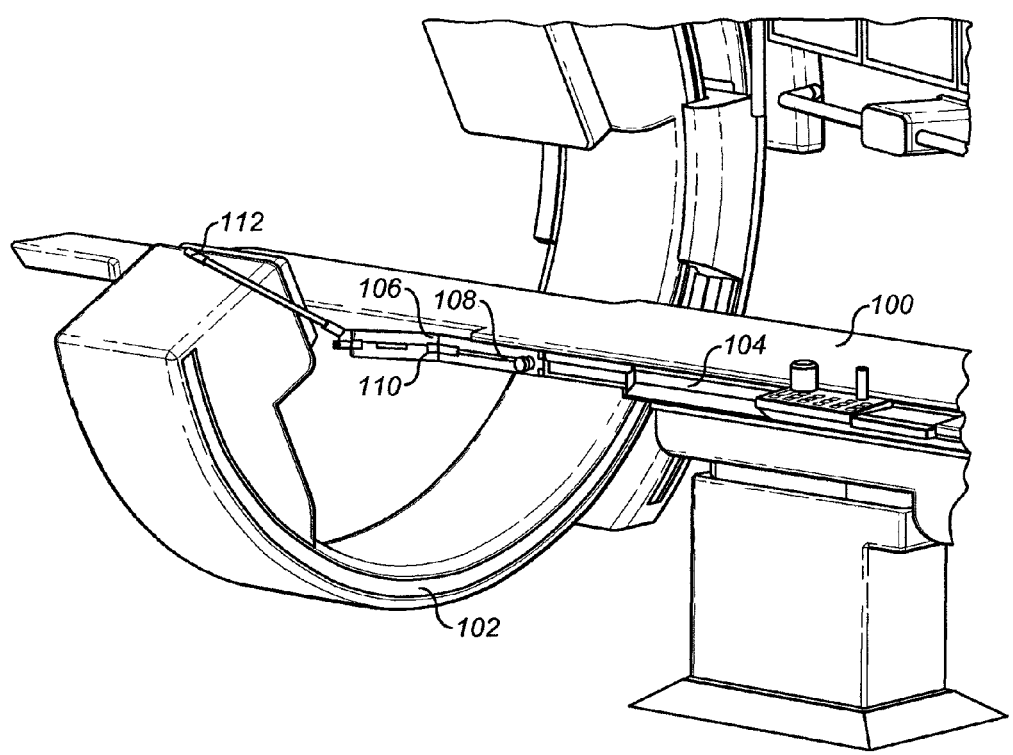
FIG. 7 is an image of a shield according to the invention being collided with a C-arm.

FIG. 7 shows an X-ray procedure table 100 with an associated C-arm 102 and having attached to its accessory rail 104 is a shield support bar 106 according to the invention.

The shield support bar 106 can be seen to comprise a horizontal support bar 108 hinged in its middle with horizontal hinge 110 and having a second support bar 112. Second support bar 112 is of the type shown in FIG. 5a. Both the horizontal support bar 108 and the second support bar 112 are intended to have X-ray opaque curtains attached to them but they are not shown in this Figure for clarity.

FIG. 7 shows the C-arm 102 colliding with the second support bar 112. The second support bar 112, by virtue of its vertical and horizontal hinges, rises up with the colliding C-arm and provides little resistance. No damage of the equipment occurs and the procedure is not interrupted.

The invention claimed is:

1. An X-ray shield for a horizontal X-ray procedure table, comprising
   a horizontal support bar for attachment to a first depending X-ray opaque curtain; and
   a second support bar, wherein the second support bar being moveably attached to the horizontal support bar in a manner such that the second support bar can rotate in two orthogonal planes, while the horizontal support bar is held in a horizontal orientation.

2. The X-ray shield according to claim 1, wherein the X-ray shield is adapted for attachment to a horizontal accessory rail of the procedure table.

3. The X-ray shield according to claim 1, wherein the first depending X-ray opaque curtain is attached to the horizontal support bar.

4. The X-ray shield according to claim 1, wherein the horizontal support bar is horizontally moveable.

5. The X-ray shield according to claim 4, wherein the horizontal support bar comprises two rigid horizontal portions horizontally hinged together.

6. The X-ray shield according to claim 1, wherein the second support bar is hingedly attached to the horizontal support bar.

7. The X-ray shield according to claim 1, wherein the second support bar is attached to the horizontal support bar via a hinge mechanism that is biased to return the second support bar to a horizontal orientation under gravity.

8. The X-ray shield according to claim 1, wherein the X-ray shield is adapted so that it can be fitted to either side of the X-ray procedure table.

9. The X-ray shield according to claim 6, wherein the second support bar is attached to the horizontal support bar via a hinge mechanism that comprises a vertical hinge that permits the second support bar to rotate away from horizontal in only one chosen direction.

10. The X-ray shield according to claim 2, wherein the first depending X-ray opaque curtain is attached to the horizontal support bar.

11. The X-ray shield according to claim 2, wherein the horizontal support bar is horizontally moveable.

12. The X-ray shield according to claim 3, wherein the horizontal support bar is horizontally moveable.

13. The X-ray shield according to claim 2, wherein the second support bar is hingedly attached to the horizontal support bar.

14. The X-ray shield according to claim 3, wherein the second support bar is hingedly attached to the horizontal support bar.

15. The X-ray shield according to claim 2, wherein the second support bar is attached to the horizontal support bar via a hinge mechanism that is biased to return the second support bar to a horizontal orientation under gravity.

16. The X-ray shield according to claim 3, wherein the second support bar is attached to the horizontal support bar via a hinge mechanism that is biased to return the second support bar to a horizontal orientation under gravity.

17. The X-ray shield according to claim 2, wherein the X-ray shield is adapted so that it can be fitted to either side of the X-ray procedure table.

18. The X-ray shield according to claim 3, wherein the X-ray shield is adapted so that it can be fitted to either side of the X-ray procedure table.

19. The X-ray shield according to claim 7, wherein the second support bar is attached to the horizontal support bar via a hinge mechanism that comprises a vertical hinge that permits the second support bar to rotate away from horizontal in only one chosen direction.

20. The X-ray shield according to claim 8, wherein the second support bar is attached to the horizontal support bar via a hinge mechanism that comprises a vertical hinge that permits the second support bar to rotate away from horizontal in only one chosen direction.

* * * * *